US00PP31702P3

(12) United States Plant Patent
Louzada et al.

(10) Patent No.: US PP31,702 P3
(45) Date of Patent: Apr. 28, 2020

(54) GRAPEFRUIT TREE NAMED 'TR-1'

(50) Latin Name: ***Citrus* x *paradisi* Macfad**
Varietal Denomination: TR-1

(71) Applicant: Texas A&M University System, College Station, TX (US)

(72) Inventors: Eliezer Silva Louzada, McAllen, TX (US); Hilda Sonia del Rio, Edinburg, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/932,036

(22) Filed: Jan. 26, 2018

(65) Prior Publication Data

US 2019/0239407 P1 Aug. 1, 2019

(51) Int. Cl.
*A01H 5/08* (2018.01)
*A01H 6/78* (2018.01)

(52) U.S. Cl.
USPC ..... Plt./201
CPC ..... *A01H 6/785* (2018.05)

(58) Field of Classification Search
USPC ..... Plt./201
CPC ..... A01H 6/785; A01H 5/08
See application file for complete search history.

*Primary Examiner* — Keith O. Robinson
(74) *Attorney, Agent, or Firm* — Dentons US LLP

(57) ABSTRACT

The new grapefruit 'TR-1' is provided. The variety is produced from a mutation of 'Rio Red' grapefruit, which can be distinguished by its outstanding features. TR-1 is a red grapefruit variety originated as a budsport mutation from Rio Red grapefruit and differentiating from the Rio Red grapefruit by a Red external color contrasting to the yellow with red blush from Rio Red grapefruit. The internal color is red with milder flavor reduced bitter taste.

4 Drawing Sheets

Latin name of the genus and species:
Genus—*Citrus.*
Species—*Citrus* x *paradisi* Macfad.
Variety denomination: The new grapefruit tree claimed is of the variety denominated 'TR-1'.

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to a new and distinct variety of grapefruit (*Citrus* x *paradisi* Macfad), which has been given the variety denomination of 'TR-1'. The new grapefruit variety 'TR-1' originated in Weslaco, Tex., USA in 2004 as a budsport mutation from a 'Rio Red' Grapefruit tree (not patented) in Weslaco, Tex. 78596. Budwood was taken from the budsport branch and grafted on C-22 bitter orange ('Swingle' trifoliata x 'Sunki' mandarin) rootstock (not patented) in a greenhouse located in Weslaco, Tex. 'TR-1' was planted in Weslaco, Tex. 78596 and observed for several generations and found to be stable.

SUMMARY OF THE INVENTION

Comparing "TR-1" to 'Rio Red' grapefruit, the external color of 'Rio Red' tends to yellow with red blush, while 'TR-1' tends to red color. The 'TR-1' internal quality differs from 'Rio Red' having mild flavor and reduced bitterness.

BRIEF DESCRIPTION OF THE DRAWINGS

The accompanying photographic illustration shows typical specimens in full color of the foliage (FIG. 4) and fruit of the new variety 'TR-1' (FIG. 1 and FIG. 2) field grown for seven years, planted in 2010 (the age of the plant shown in the pictures was about 7 years old). The colors are as nearly true as is reasonably possible in a color representation of this type.

FIG. 4 is a photograph of a seven year old TR-1 tree showing the foliage.

Figure 1:
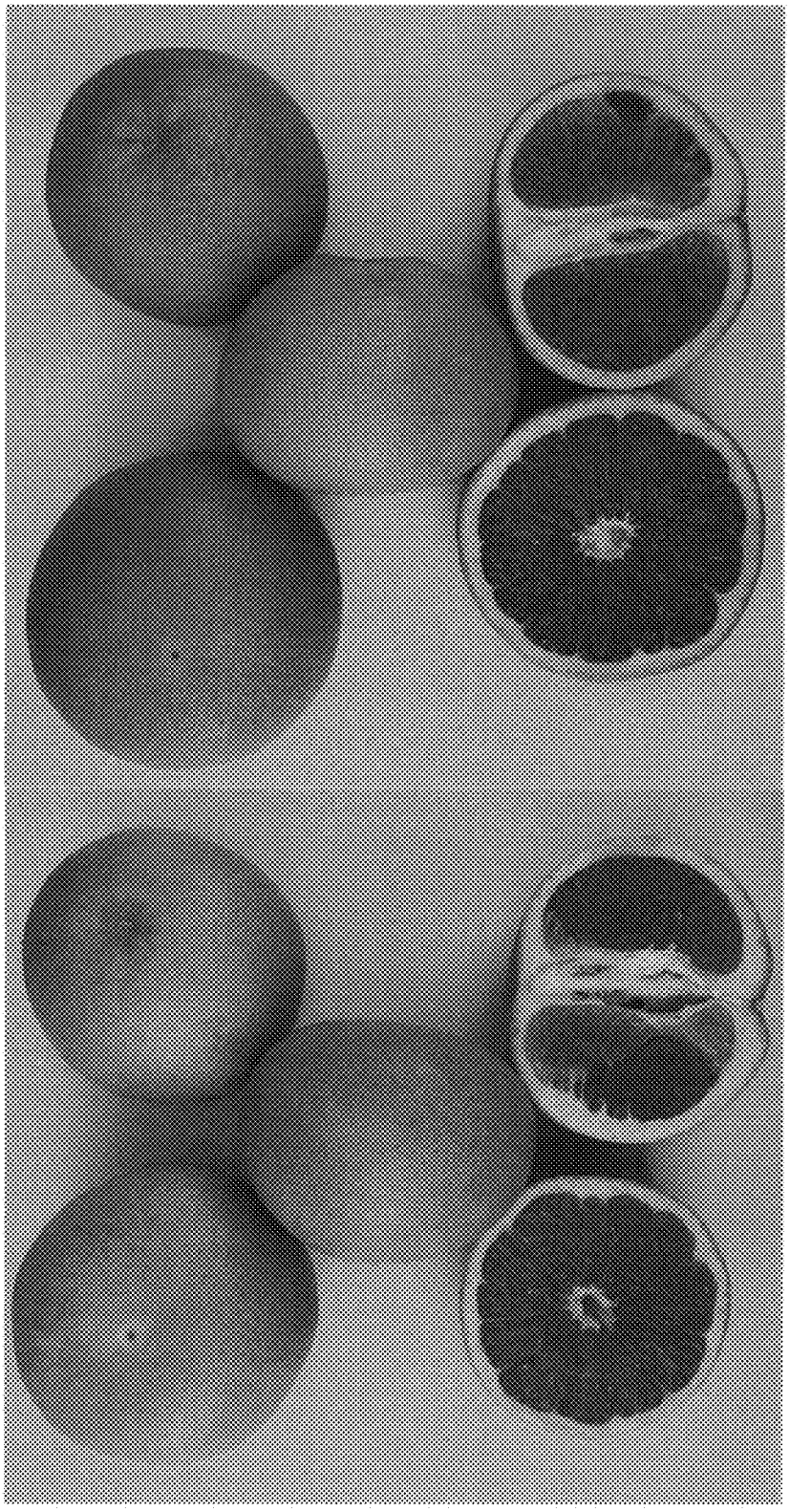
FIG. 1 is a photograph of 'Rio Red' grapefruit fruit (left) and 'TR-1' grapefruit fruit (right) harvested December 2017 from field grown seven year old tree.
Figure 2:
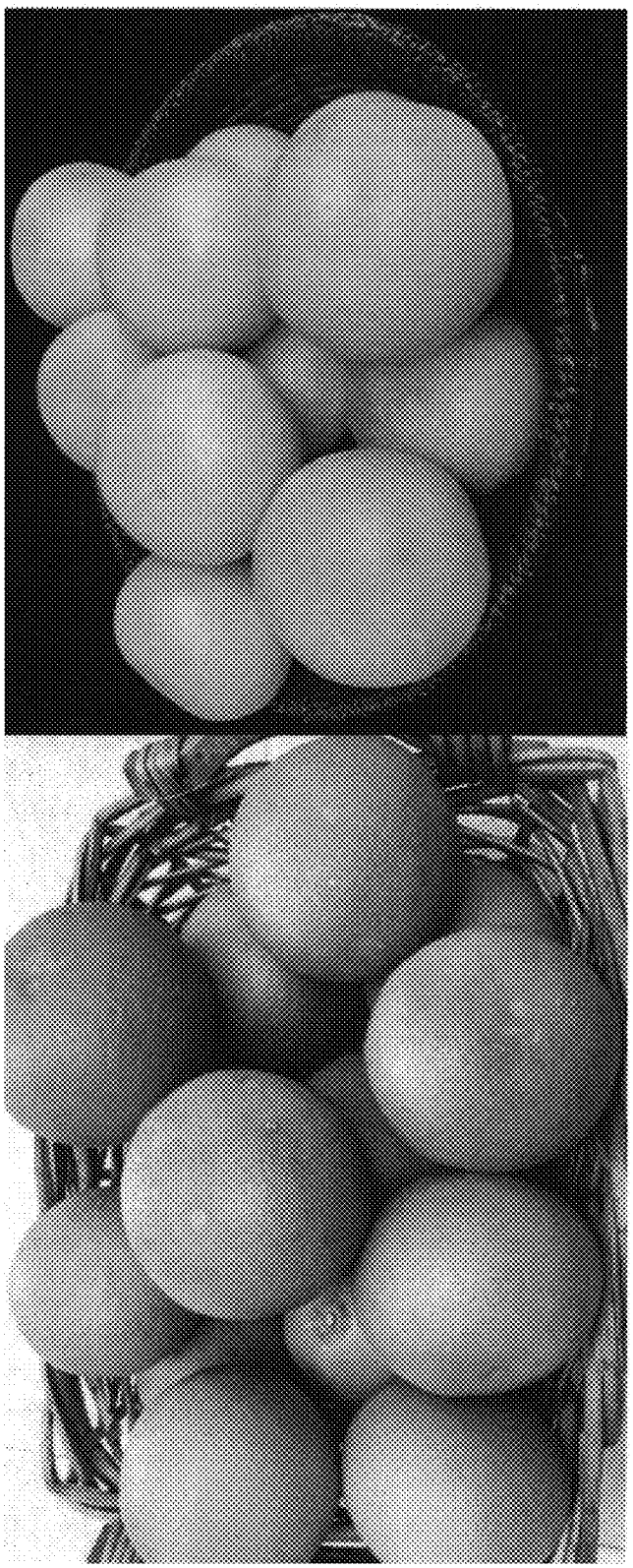
FIG. 2 is a photograph of 'TR-1' non-degreened fruits (left) and degreened* (right), harvested October 2017 from field grown seven year old tree. *Treated with ethylene.
Figure 3:
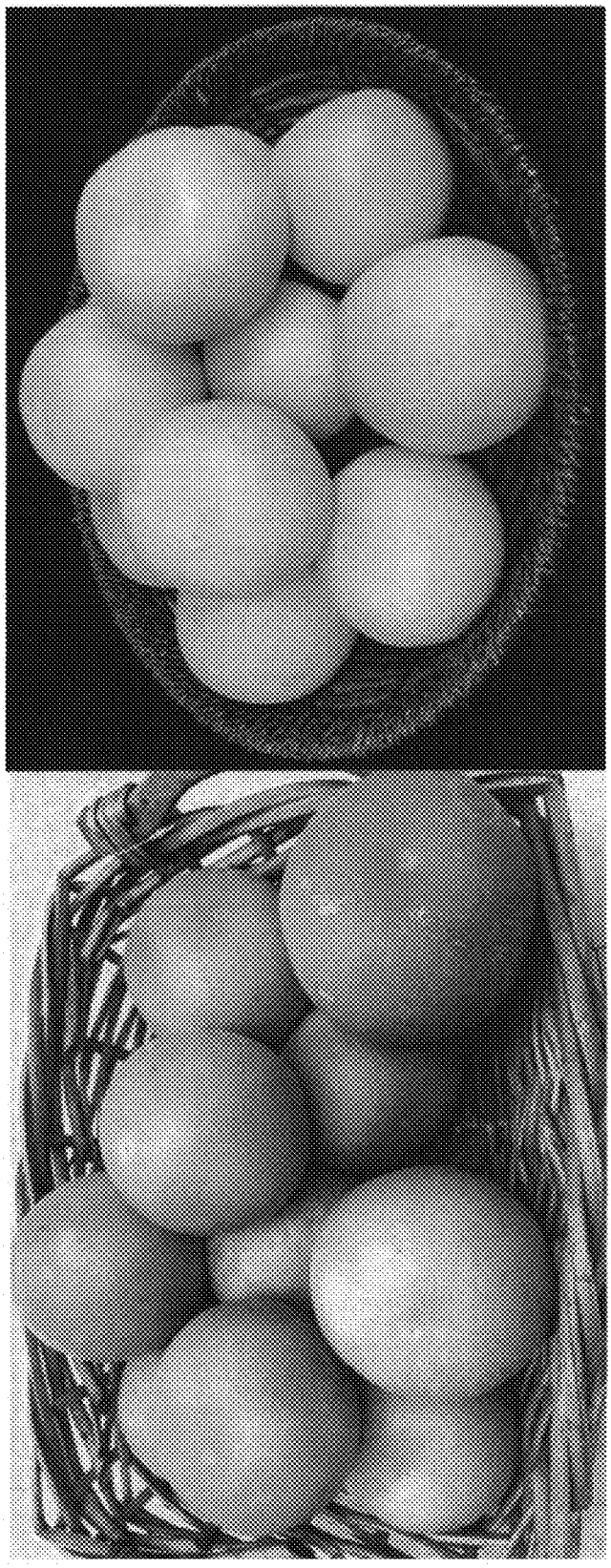
FIG. 3 is a photograph of 'Rio Red' grapefruit non-degreened fruits (left) and degreened* (right), harvested October, 2017 from field grown seven year old tree. *Treated with ethylene.

The colors in the photographs are as close as possible with the photographic and printing technology utilized. The color values cited in the detailed botanical description accurately describe the colors of the new grapefruit.

DETAILED BOTANICAL DESCRIPTION

The following detailed description sets forth the distinctive characteristics of 'TR-1'. The claimed plant was asexually propagated by grafting buds of TR-1 to C-22 bitter orange ('Swingle' trifoliata x 'Sunki' mandarin) rootstock in a greenhouse located in Weslaco, Tex. After grafting, the trees were grown in the greenhouse for 18 months and planted in Weslaco, Tex. 'TR-1' was grown around seven years in the field at the moment of data collection.

Dimensions, sizes, colors, and other characteristics are approximations and averages set forth as accurately as possible. Descriptions or characteristics were taken on trees approximately 7 years of age, and the descriptions relate to trees grown in Weslaco, Tex.

Color notations provided herein are made according to The Royal Society Horticultural Colour Chart, 2015, Sixth Edition.

It should be understood that characteristics described will vary somewhat depending on cultural practices, rootstock used, and climatic conditions and can vary with location and season. Quantified measurements are expressed as an average taken from a number of individual plants of the new variety. The measurement of any individual plant or any group of plants, of the new variety may vary from stated average. The characteristic observed of the fruits being produced inside of the canopy when using C-22 bitter orange rootstock may vary according to the rootstock used.

Classification:

a. *Genus.*—*Citrus.*
b. *Species.*—*Paradisi.*
c. *Common name.*—Grapefruit.

Tree:

*Vigor.*—Vigorous.
*Density of canopy.*—Dense.
*Growth habit.*—Compact growth.
*USDA zone.*—9, 10.
*Height.*—3.75 M.
*Trunk diameter.*—(At 30 cm above the graft): 39.55 cm.
*Bark texture.*—Smooth.
*Bark color.*—Yellowish Gray 156 A&B.
*Tendency toward alternative bearing.*—No.
*Crotch angle.*—45°.
*Branches bark color.*—Light Olive Gray 197 C&D.
*Bark texture.*—Smooth.
*Thorns present?.*—Yes (small, younger branches only).
*Thorn length.*—0.5 cm (younger branches only).
*Current year shoot color.*—Yellow Green 147 B&C.

Leaves:

*Length.*—10.76 cm.
*Width.*—5.17 cm.
*Ratio of length:width.*—2:1.
*Blade margin.*—Light to moderate crenate.
*Leaf shape.*—Oval.
*Apex shape.*—Acute.
*Shape of base of leaf.*—Acute to Obtuse.
*Leaf texture, upper.*—Glabrous.
*Leaf texture, lower.*—Midrib with bronchided secondary veins forming secondary loops and arches never reaching the margin of the leaf.
*Color of upper surface.*—Grayish Olive Green 137 A&B.
*Color of bottom surface.*—Moderate Yellow Green 146 C&D.
*Petiole length.*—1.33 cm.
*Petiole diameter.*—0.84 cm.
*Petiole color upper.*—Grayish Olive Green 137 A&B.
*Petiole color bottom.*—Moderate Yellow Green 146 C&D.
*Wings present.*—Yes.
*Wings width.*—1.25 cm.
*Anthocyanin coloration in young leaves.*—Not present.

Flower:

*Flowering habit.*—Once a year.
*Flowering period.*—Middle February to beginning April.
*Flower bud length.*—1.67 cm.
*Flower bud width.*—0.76 cm.
*Flower bud color.*—White NN155 B&C.
*Flower bud shape.*—Rounded to Oblong.
*Flower length.*—2.51 cm.
*Flower diameter.*—3.52 cm.
*Number of petals.*—4.5.
*Shape of petals.*—Oval.
*Petal length.*—1.89 cm.
*Petal width.*—0.69 cm.
*Petal color.*—White NN 155 B Thru D.
*Petal margin.*—Smooth.
*Petal apex.*—Acute.
*Sepal length.*—0.45 cm (Gamosepals with 4-5 apex).
*Sepal width.*—0.7 cm.
*Sepal color.*—Pale Yellow Green 149 D.
*Sepal apex.*—Acute.
*Sepal margin.*—Smooth.
*Pedicel length.*—1.16 cm.
*Pedicel color.*—Light Yellow Green N144 D.
*Pistil length.*—1.2 cm.
*Pistil color.*—Greenish white 157 D.
*Style length.*—0.95 cm.
*Style color.*—Light Yellow Green 150 D.
*Anther length.*—3 mm.
*Anther color.*—Moderate Yellow 162 A & B.
*Stigma color.*—Strong Greenish Yellow 151A & 153 A.
*Ovary color.*—Strong Yellow Green N144 A & B.
*Stamen per flower.*—27.
*Stamen length.*—1.2 cm.
*Length of filament.*—1.2 cm.
*Amount of pollen.*—Abundant.
*Color of pollen.*—Moderate Yellow 162 A & B.

Fruit:

*Fruit location on tree.*—Inside of the canopy.
*Quantity per cluster.*—10.
*Axial diameter.*—11.5 cm.
*Apical diameter.*—10.15 cm.
*Weight.*—466.96 g.
*General shape.*—Spherical to Oblate.
*Position of the broadest part of the fruit.*—At the middle.
*Navel.*—Absent.
*Oil glands per cm$^2$.*—43.8.
*Oil gland diameter.*—1 mm.
*Peel thickness.*—5.5 mm.
*Ease of peeling.*—Moderate to difficult.
*Rind texture.*—Smooth.
*Albedo thickness.*—3.5 mm.
*Albedo color.*—Light Yellowish Pink 29 C & D.
*Quantity of fruit segments per fruit.*—12.2.
*Toughness of segments membrane.*—Moderate.
*Juice sac length.*—1.83 cm.
*Juice sac shape.*—Elongated.
*Juice sac length to width ratio.*—6:1.
*Juice sac color.*—Moderate Red 180 C&D.
*Juice color.*—Moderate Red 180 B through D.
*Juice soluble solids.*—(Brix): 9.15.

*Sugar acid ratio.*—14 (in January).
*Relative harvest maturity.*—Mid-late season.
*Harvest window.*—October to March.
*External color.*—Vivid Reddish Orange 34 A thru C.
*Internal color.*—Vivid Red 45 A Thru D.
*Seeds present.*—2.75 seeds.
*Polyembrony of the seed.*—Present.
*Seed length.*—1.2 cm.
*Seed width.*—0.8 cm.
*Seed color.*—NN 155 A Yellowish White.
*Seed texture.*—Smooth.
*Parthenocarpy.*—Present.
*Market use.*—Fresh, juice and segments.
*Keeping quality.*—Good.
*Shipping quality.*—Good.

Disease and pests:

*Citrus greening* (*Candidatus liberibacter asiaticus*).—Sensitive.
*Other diseases.*—Not been tested.
*Pests.*—Not been tested.

The invention claimed is:

1. A new and distinct variety of grapefruit named 'TR-1', substantially as illustrated and described herein.

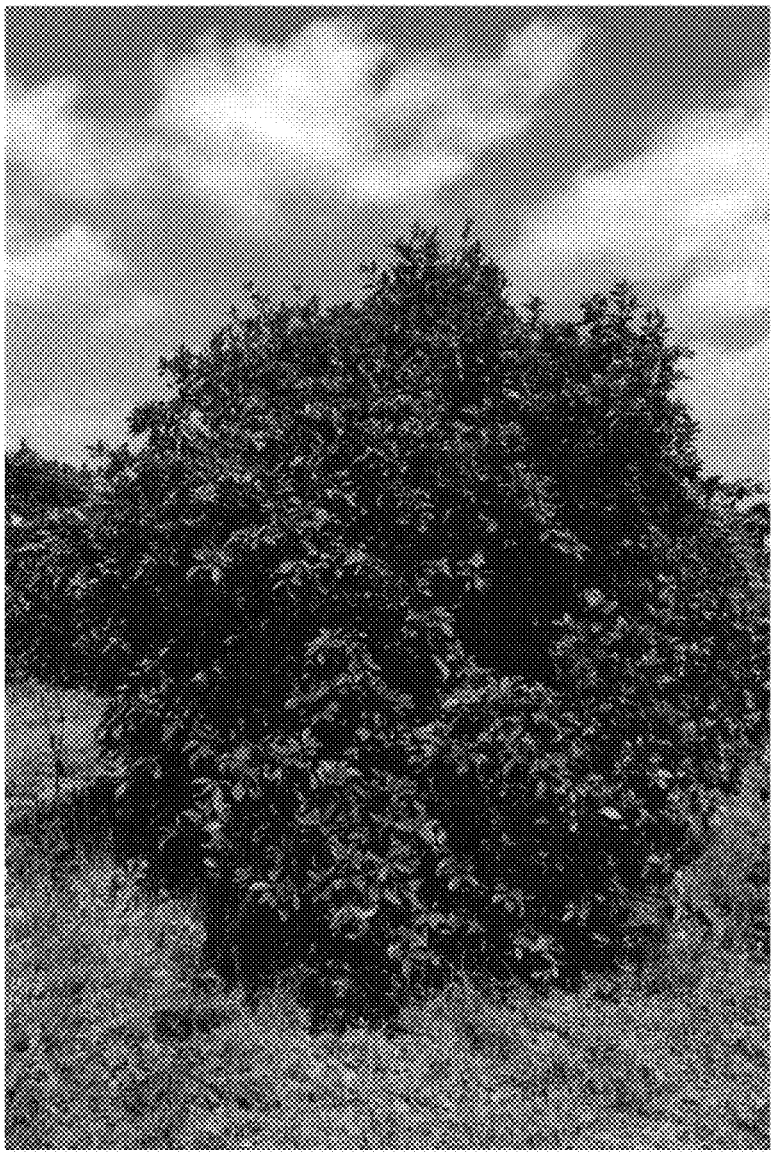

* * * * *